United States Patent [19]

Winter et al.

[11] Patent Number: 4,839,159

[45] Date of Patent: Jun. 13, 1989

[54] TOPICAL L-CARNITINE COMPOSITION

[75] Inventors: Susan C. Winter, Fresno; Stefan Szabo-Aczel, Clovis, both of Calif.

[73] Assignee: Topicarn, Inc., Fresno, Calif.

[21] Appl. No.: 153,243

[22] Filed: Feb. 8, 1988

[51] Int. Cl.⁴ .................. A61K 7/40; A61K 7/42; A61K 7/44

[52] U.S. Cl. .................. 424/59; 424/60; 514/556; 514/844; 514/847; 514/861; 514/880; 514/886; 514/887; 514/937; 514/944; 514/969

[58] Field of Search .................. 514/556, 880, 887; 424/59

[56] References Cited

U.S. PATENT DOCUMENTS

| | | | |
|---|---|---|---|
| 4,254,147 | 3/1981 | Cavazza | 514/556 |
| 4,527,781 | 7/1985 | Goldberg et al. | 514/556 |
| 4,649,159 | 3/1987 | Fanelli | 514/556 |
| 4,752,467 | 6/1988 | Konrad et al. | 514/556 |

FOREIGN PATENT DOCUMENTS

| | | | |
|---|---|---|---|
| 0097009 | 8/1978 | Japan | 514/556 |
| 0102912 | 9/1978 | Japan | 514/556 |
| 126420 | 8/1982 | Japan | 514/556 |

OTHER PUBLICATIONS

Merck Index, 1976, p. 236.

*Primary Examiner*—Dale R. Ore
*Attorney, Agent, or Firm*—Richard L. Neeley

[57] ABSTRACT

The present invention provides a composition comprising L-carnitine in a suitable vehicle for topical application in an effective amount. The present compositions are useful in improving or healing skin conditions including wrinkling, dry or peeling skin, and burns (particularly sunburn), and in healing and prevention of scar formation, particularly that caused by infection by a pathogen. Treatment methods are also provided.

13 Claims, No Drawings

TOPICAL L-CARNITINE COMPOSITION

INTRODUCTION

1. Technical Field

The present invention relates to topical compositions useful in treating skin conditions.

2. Background

Numerous compositions are available for the treatment or prevention of skin conditions including dryness, peeling, wrinkling, and scarring due to conditions such as acne, burns (including sunburn), and aging of the skin, particularly aging due to exposure to sun. Although numerous substances have been tested as active ingredients to promote improved skin condition, only a small number of those additives have been shown to be more effective than treatment vehicle composition alone. For example, retinoic acid has been said to be useful for the treatment of acne, and a number of growth factors have been reported to be effective in the promotion of wound healing. Corticosteroids have also been shown to be effective in treating various skin problems, particularly those related to allergic or other inflammatory conditions.

It would be beneficial to find other effective additives, particularly those which could be used on a long term basis without undesirable side effects.

3. Relevant Literature

Winter et al., *AJDC* (1987) 141:660-665 describe plasma carnitine deficiency and response to therapy with L-carnitine. Goldsmith, *Biochemistry and Physiology of the Skin*, Oxford Univ. Press (1983) describes the biology and biochemistry of the skin and energy metabolism of the skin. Fitzpatrick et al., *Dermatology and General Medicine*, 2nd Ed., McGraw Hill Book Company, (1979) and Ardnt et al., *Manual of Dermatologic Therapy*, 3rd Ed., Little Brown and Co., (1983) describe skin diseases and treatment thereof but make no specific references to L-carnitine therapy or the action of L-carnitine on skin. Craig et al., Eds. *Modern Pharmacology*, Little Brown and Co., Boston, (1982) describe the properties and actions of carnitine but makes no reference to skin metabolism. Szabo et al., *American Society of Human Genetics*, Philadelphia, Pa., November 1986, describe L-carnitine supplementation of tissue culture media for in vitro cultivation of human fibroblasts and amniocytes.

SUMMARY OF THE INVENTION

The present invention provides a composition comprising L-carnitine in a vehicle suitable for topical application to the skin of a mammal. The present compositions are useful in improving or preventing deleterious skin conditions, especially epidermal exfoliation and loss of skin elasticity. Treatment methods are also provided.

DESCRIPTION OF THE SPECIFIC EMBODIMENTS

A topical composition useful for improving or healing a number of skin conditions related to epidermal exfoliation and loss of elasticity is provided. The composition comprises L-carnitine in a suitable vehicle for topical application.

L-carnitine, also known as $\gamma$-trimethylamino-$\beta$-hydroxybutyrate or Vitamin $B_T$, is a normal endogenous intermediary metabolite present in blood, urine and all cells of animals. L-carnitine has dual functions in lipid metabolism, transporting fatty acids and other acylated compounds across the inner mitochondrial membrane and maintaining the acyl CoA/free CoA ratio between the mitochondria and the cytosol. Carnitine readily forms esters with CoA compounds and thus can remove such compounds from the cell during abnormal metabolic conditions.

Although the exact mechanism of action of L-carnitine in alleviating skin disorders is unknown, it is suspected to be related to metabolism of the skin, which is highly lipid dependent. The increased distance between the blood supply and the maturing cells of the epidermis makes glucose unavailable as the principal substrate for adenosine triphosphate (ATP) production or other high-energy phosphate production. The glycogen content of epidermal cells is low and the fat content high, making the mitochondrial oxidation of fat the principal fuel source.

Deficiency states of carnitine have been described as associated with specific clinical symptoms. These include hepatic dysfunction, encephalapathy, progressive muscle weakness with fatty muscle on biopsy, cardiomyopathy, and failure to thrive. Reversal of abnormal symptomatology of these disorders has been shown to occur with administration of L-carnitine. However, use in topical applications for skin care was not previously known.

It has now been found that application of topical compositions containing L-carnitine are useful to improve or heal a variety of deleterious skin conditions related to epidermal exfoliation and loss of elasticity. L-carnitine can be used to treat dry, peeling, scarred, or wrinkled skin irrespective of the cause of the particular condition. For example, L-carnitine has been successfully used to improve healing and to minimize scar formation due to varicella infection. It has also been used to improve dryness and peeling due to sunburn and to improve skin elasticity.

L-carnitine can be synthesized according to the method described by Tomita et al., *J. Physiol. Chem.* (1927) 169:263. In addition, it is commercially available from a number of sources including Sigma-Tau (an Italian supplier), Sigma Chemical Co. (St. Louis, Mo.), and Aldrich Chemical Co., Inc. (Milwaukee, Wis.). L-carnitine can be presented as a pure enantiomer or as a mixture of enantiomers (i.e., DL-carnitine). The amounts of carnitine set forth below as examples of dosages and concentrations in solution refer to the active ingredient, L-carnitine.

Carnitine will typically be presented in a physiologically acceptable carrier for application to the affected area. Both aqueous and non-aqueous solutions and suspensions are suitable. The nature of the carriers may vary widely and can be adapted to the intended location or duration of application. Creams, gels, lotions, ointments, suspensions, and emulsions are all suitable. Aqueous solutions (including water, saline solutions, and buffered saline solutions) are preferred for most applications. Such uses include acne medications where application of additional oil to the skin is not desired. Additionally, a non-staining aqueous solution can be applied under clothes or to other areas where a water-oil base composition may be less desirable. It should be noted that a simple water solution of carnitine is not a composition of the invention if it is not pharmacologically acceptable due to the presence of pyrogens or any other substance. Pharmacologically acceptably aqueous solutions generally require special care in their preparation, as is well understood in the art.

A cream or ointment base for topical application to the skin also finds use and is frequently preferable. This is paricularly true where the composition is used on dry or peeling skin and when a moisturing vehicle may otherwise be desirable. Suitable bases include lanolin, Silvadene (Marion), particularly for treatment of burns, Aquaphor (Duke Laboratories, South Norwalk, Conn.), and like bases. If desired, it is possible to incorporate either aqueous or water-oil base compositions in bandages or other wound dressings to provide for continuous exposure of the affected area to L-carnitine. Aerosol applicators may also find use.

The concentration of L-carnitine in the treatment composition is not critical as long as sufficient active material is present to provide demonstratable affects. Usually L-carnitine will be present at from at least about 1 to about 20% w/w. L-carnitine will usually be present in a liquid vehicle at concentrations from about 0.01 to 1.0 g/ml, more usually from about 0.05 to 0.15 g/ml, most usually at about 0.1 g/ml. When the vehicle is an ointment, a lotion or a cream, L-carnitine is present at from about 1 to 25% w/w, more usually from about 1 to 15%, most usually at about 10%.

Optionally, effective amounts of other additives may be combined with the compositions of the present invention. For example, when the composition is used to treat skin conditions susceptible to or involving infectious agents, such as wounds or acne, an antiseptic agent can be added. Such agents include antibacterial agents, including those used to treat acne, and antifungal or other antiseptic agents. Additionally, L-carnitine can be added to sun block, sun screen, and post-tanning preparations; to acne treatment preparations not containing antiseptics; to moisturizers; to makeup formulations; and to like compositions intended for application to the skin for other purposes. A bacteriostatic agent may be included in the composition to prevent bacterial contamination, as a carnitine composition is a good culture medium for bacteria.

The compositions will be applied topically to an affected area of skin. Usually the compositions will be applied daily for at least several days. However, more frequent application is also contemplated. For example, in the treatment of injured tissue, such as a rash, acne, or a pathogen-induced skin problem, it may be desirable to continuously maintain the treatment composition on the affected area during healing, with applications of the treatment composition from two to four times a day or more frequently. Use may also be for extended periods, including years. No adverse side effects from such extended use were observed in a human test subject using L-carnitine solution daily for over a year.

The present invention provides, in addition to compositions as described above, a method for improving deleterious skin conditions. The method comprises applying L-carnitine to an affected area. The method promotes healing and minimizes scarring of the skin following injuries such as injury due to burns, including sunburn; acne; contact dermatitis; and infection due to a pathogen, e.g., bacteria, such as *Stapholoccocal aureus*, or a virus such as varicella or herpes simplex.

Although the compositions and methods are most commonly used with humans and the treatment of human skin, treatment of skin of other mammals is also contemplated. For example, animal disorders resulting in exfoliation or a loss of skin elasticity, such as mange, can be treated by a composition of the invention. In addition to use with humans, carnitine can be administered to the skin of animals, particularly domestic animals such as dogs, cats, horses, and cattle.

It should be emphasized that the invention is not intended to treat the primary disorder but rather affects epidermal exfoliation and/or loss of skin elasticity that result from the primary effects, such as burn injury or infection. The compositions and method of the invention are useful both as treatments and as prophylactics.

When the method is being practiced, the manner in which carnitine is administered to the affected area is immaterial to the practice of the invention. Although application will generally occur by using carnitine in a topical manner, other forms of administration, such as oral ingestion and/or intraveneous or other types of injection, can also be used. The following experimental results are offered by way of example and not by way of limitation.

EXPERIMENTAL

Example 1

Reduction of Scarring from Varicella Infection

The test subject was a 26-year-old woman who had severe varicella (chicken pox) with multiple pox marks on her face. Pox marks were equal per side prior to treatment. After the scabbing had ended, L-carnitine solution at a concentration of 1 gram/10 ml in water was applied twice daily to the right side of her face only. The subject experienced improved healing and less scar formation on the treated (right) side of her face than on the untreated (left) side as determined by two physician observers and two lay observers.

EXAMPLE 2

Reduction of Peeling from Sunburn

The subject was a 37-year-old healthy woman who sustained a first-degree sunburn on her forehead and face. Three days after exposure to the sun, significant peeling of the skin was observed. An L-carnitine solution at a concentration of 1 gram/10 ml in water was applied at least twice daily to the affected area. Complete healing of the skin and a cessation of peeling was experienced within 48 hours of the first application as confirmed by two physician observers and one lay observer.

EXAMPLE 3

Reduction of Rate of Wrinkle Appearance

A 33-year-old caucasian woman was treated for facial wrinkles around her eyes. L-carnitine solution at a concentration of 1 gram/10 ml of a cream base was applied daily for a period of one year. A decrease in the number of wrinkles around her eyes was noted by two physician observers and the subject after a few weeks of trial. After one year of treatment, the subject had experienced no new wrinkles in the treated area as observed by two physicians and the subject.

All publications mentioned in this specification are indicative of the level of skill of those skilled in the art to which this invention pertains. All publications are herein incorporated by reference to the same extent as if each individual publication was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A topical composition for improving or preventing deleterious skin conditions comprising an effective amount of L-carnitine in a pharmacologically acceptable vehicle for topical application selected from the group consisting of ointments, lotions, gels, suspensions, emulsions and creams.

2. The composition of claim 1, wherein said concentration is from 5 to 15 % w/w.

3. The composition of claim 1, wherein carnitine is present at a concentration of from 1 to 25 % w/w.

4. The composition of claim 1, wherein said composition additionally comprises an antiseptic.

5. The composition of claim 1, wherein said antiseptic is an antibacterial agent.

6. The composition of claim 1, wherein said composition additionally comprises a sunscreen agent.

7. A method for improving a deleterious skin condition comprising administering an effective amount of L-carnitine to an area of skin affected by said condition.

8. The method of claim 7, wherein said condition is dry or peeling skin.

9. The method of claim 7, wherein said condition is loss of skin elasticity.

10. The method of claim 7, wherein said condition is an injury to said skin.

11. The method of claim 10, wherein said injury is due to acne, to a burn, or to infection by a pathogen.

12. The method of claim 11, wherein said pathogen is a virus.

13. The method of claim 7, wherein said administering comprises applying L-carnitine to said area in a topical composition.

* * * * *